US012693283B2

(12) United States Patent
Stewart et al.

(10) Patent No.: US 12,693,283 B2
(45) Date of Patent: Jul. 28, 2026

(54) ELECTROCHEMICAL SENSOR ASSEMBLY AND SYSTEM

(71) Applicant: Evoqua Water Technologies LLC, Pittsburgh, PA (US)

(72) Inventors: Justin W. Stewart, Sarasota, FL (US); Calvin Horst, Bradenton, FL (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 687 days.

(21) Appl. No.: 17/920,048

(22) PCT Filed: Feb. 12, 2021

(86) PCT No.: PCT/US2021/017749
§ 371 (c)(1),
(2) Date: Oct. 20, 2022

(87) PCT Pub. No.: WO2021/216172
PCT Pub. Date: Oct. 28, 2021

(65) Prior Publication Data
US 2023/0273170 A1      Aug. 31, 2023

Related U.S. Application Data

(60) Provisional application No. 63/027,605, filed on May 20, 2020, provisional application No. 63/013,698, filed on Apr. 22, 2020.

(51) Int. Cl.
*G01N 33/18*          (2006.01)
(52) U.S. Cl.
CPC ..... *G01N 33/1893* (2013.01); *G01N 33/1826* (2013.01)

(58) Field of Classification Search
None
See application file for complete search history.

(56) References Cited

U.S. PATENT DOCUMENTS

| 7,424,399 B2 | 9/2008 | Kahn et al. |
| 2009/0123340 A1 | 5/2009 | Knudsen et al. |
| 2019/0336963 A1 | 11/2019 | Samproni |

FOREIGN PATENT DOCUMENTS

| WO | 2018013845 A1 | 1/2018 |
| WO | 2019218395 A1 | 11/2019 |

OTHER PUBLICATIONS

International Search Report, corresponding PCT/US21/17749, dated Apr. 26, 2021.

(Continued)

*Primary Examiner* — Daniel S Larkin

(57) ABSTRACT

A sensor assembly having a housing including a plurality of compartments, an actuator for selectively hermetically sealing or fluidly connecting the plurality of compartments, a plurality of sensors each positioned in a corresponding compartment, and a receiver is disclosed. A method of monitoring a parameter of a fluid in a remote location is also disclosed. The method includes deploying the sensor assembly to the remote location, fluidly connecting a first sensor to the fluid, transmitting to an external controller data including values for the measured parameter of the fluid, and operating the actuator to fluidly connect a second sensor responsive to the operating interval of the first sensor trending to expiration. A sensing system having a sensor assembly and an external controller is also disclosed. A method of facilitating monitoring a parameter of the fluid in a remote location by providing the sensor assembly is also disclosed.

28 Claims, 8 Drawing Sheets

(56)            References Cited

OTHER PUBLICATIONS

Abou-Antoun, Patrick, "Requisition by The Examiner", Canadian
Patent Application No. 3175535, mailed Jan. 29, 2026, 3 pages.

3000

4000

1001

2001

220

300

330

302

304

ELECTROCHEMICAL SENSOR ASSEMBLY AND SYSTEM

CROSS-REFERENCE TO RELATED APPLICATIONS

This application is a U.S. National Phase application and claims the benefit of priority under 35 U.S.C. § 371, of International (PCT) Patent Application Serial No. PCT/US2021/017749, filed Feb. 12, 2021, which claims priority under 35 U.S.C. § 119(e) to U.S. Provisional Application Ser. No. 63/013,698, titled "Method for Extending the Life of Electrochemical Sensors" filed Apr. 22, 2020 and U.S. Provisional Application Ser. No. 63/027,605, titled "Method for Extending the Life of Electrochemical Sensors" filed May 20, 2020, each of which is incorporated herein by reference in its entirety for all purposes.

FIELD OF TECHNOLOGY

Aspects and embodiments disclosed herein are generally related to sensor assemblies, and more specifically, to sensor assemblies for monitoring a parameter of a fluid in a remote location.

SUMMARY

In accordance with one aspect, there is provided a sensor assembly. The sensor assembly may comprise a housing, an actuator, a plurality of sensors, and a transmitter. The housing may comprise a plurality of compartments capable of being reversibly hermetically sealed or fluidly connected to a source of a fluid. The actuator may be configured to selectively hermetically seal or fluidly connect each compartment of the plurality of compartments. The plurality of sensors may be configured to measure a parameter of the fluid. Each sensor of the plurality of sensors may be positioned in a corresponding compartment of the plurality of compartments. The transmitter may be operably connected to the plurality of sensors. The transmitter may be operably connectable to an external controller.

In some embodiments, each of the plurality of sensors may be gas analyzers.

In some embodiments, the gas analyzers may be configured to measure concentration of at least one of hydrogen sulfide, benzene, ammonia, carbon monoxide, carbon dioxide, oxygen, and methane in the fluid.

In some embodiments, the plurality of sensors may be selected from gas analyzers, temperature sensors, humidity sensors, pH sensors, conductivity sensors, oxidation-reduction potential (ORP) sensors, total suspended solids (TSS) sensors, total dissolved solids (TDS) sensors, liquid chemical sensors, dissolved gas sensors, and flow meters.

The sensor assembly may have one compartment fluidly connected to the source of the fluid.

The sensor assembly may have more than one compartment fluidly connected to the source of the fluid.

In some embodiments, the plurality of sensors may be configured to selectively measure more than one parameter of the fluid.

The sensor assembly may be operably connectable to the external controller by one or more of ultra-high frequency (UHF) radio waves, a cellular network data connection, and a wireless local area network (WLAN).

The actuator may be configured to operate on a pre-determined schedule.

In some embodiments, the transmitter may be configured to transmit data from the plurality of sensors to a memory storing device coupled to the external controller.

The sensor assembly may further comprise a receiver operably connected to the actuator and operably connectable to the external controller. In some embodiments, the actuator may be configured to operate responsive to the sensor assembly receiving a signal from the external controller.

In accordance with another aspect, there is provided a method of monitoring a parameter of a fluid in a remote location. The method may comprise deploying a sensor assembly to the remote location. The sensor assembly may comprise a plurality of sensors configured to measure the parameter of the fluid and an actuator configured to selectively fluidly connect each sensor to the fluid. The method may comprise fluidly connecting at least one first sensor of the plurality of sensors to the fluid to measure the parameter of the fluid. The method may comprise transmitting to an external controller data comprising values for the measured parameter of the fluid. The external controller may be configured to determine an operating interval of the at least one first sensor responsive to the data. The method may comprise operating the actuator to fluidly connect at least one second sensor of the plurality of sensors to the fluid on a pre-determined schedule or responsive to the external controller determining the operating interval of the at least one first sensor is trending to expiration.

In some embodiments, the sensor assembly comprises a housing having a plurality of compartments capable of being reversibly hermetically sealed or fluidly connected to the fluid, each sensor of the plurality of sensors positioned in a corresponding compartment of the plurality of compartments, and the actuator being configured to selectively hermetically seal or fluidly connect each sensor by hermetically sealing or fluidly connecting each compartment.

The method may further comprise monitoring the data for the measured parameter of the fluid.

The method may further comprise modifying the fluid responsive to the values for the measured parameter exceeding a threshold value.

The method may comprise operating the actuator to fluidly connect the at least one second sensor to the fluid prior to the pre-determined schedule or the external controller determining the operating interval of the at least one first sensor is trending to expiration.

The method may comprise calibrating or the at least one first sensor with a measurement taken by the at least one second sensor.

The method may comprise alerting a user responsive to the external controller determining the operating interval of at least one last sensor is trending to expiration.

The method may comprise collecting the deployed sensor assembly from the remote location.

The method may comprise deploying a substitute sensor assembly to the remote location.

In accordance with another aspect, there is provided a sensing system. The sensing system may comprise a sensor assembly comprising a housing comprising a plurality of compartments capable of being reversibly hermetically sealed or fluidly connected to a source of a fluid, an actuator configured to selectively hermetically seal or fluidly connect each compartment of the plurality of compartments, a plurality of sensors configured to measure a parameter of the fluid, each sensor of the plurality of sensors positioned in a corresponding compartment of the plurality of compartments, a transmitter operably connected to the plurality of sensors, and a receiver operably connected to the actuator.

The sensing system may comprise an external controller operably connectable to the transmitter and the receiver. The external controller may be configured to receive data from the transmitter comprising values for the measured parameter of the fluid. The external controller may be configured to transmit a signal to the receiver providing operating instructions for the actuator responsive to the data.

In some embodiments, the external controller may be a mobile computing device.

In some embodiments, the mobile computing device may be connectable to the sensor assembly by at least one of ultra-high frequency (UHF) radio waves, a wireless local area network (WLAN), and a cellular network data connection.

In some embodiments, the mobile device may be configured to automatically connect to the transmitter upon entering the wireless personal area network (WPAN) of the receiver.

In some embodiments, the sensor assembly and the external controller may be connectable to a cloud.

In some embodiments, the sensor assembly may be connectable to the cloud by cellular network data connection.

In some embodiments, the external controller may be configured to alert a user responsive to the data indicating a need to repair or replace the sensor assembly or one or more components thereof.

In some embodiments, the external controller may be configured to alert a user responsive to the values for the measured parameter exceeding a threshold value or being outside tolerance of an expected theoretical measurement.

In some embodiments, the external controller may be connectable to a treating station disposed remotely from the sensor assembly. The treating station may be configured to modify the fluid responsive to the values for the measured parameter.

Each of the plurality of sensors may be configured to measure concentration of a target analyte in the fluid.

In accordance with another aspect, there is provided a method of facilitating monitoring a parameter of a fluid in a remote location. The method may comprise providing a sensor assembly comprising a housing comprising a plurality of compartments capable of being reversibly fluidly connected to a source of a fluid, an actuator configured to selectively fluidly connect each compartment of the plurality of compartments, a plurality of sensors configured to measure a parameter of the fluid, each sensor of the plurality of sensors positioned in a corresponding compartment of the plurality of compartments, and a transmitter operably connected to the plurality of sensors. The method may comprise providing instructions to deploy the sensor assembly to the remote location. The method may comprise providing instructions to fluidly connect the sensor assembly to the fluid.

In some embodiments, the sensor assembly may further comprise a receiver operably connected to the actuator. The method may comprise providing instructions to operably connect the sensor assembly to an external controller configured to receive data from the transmitter comprising values for the measured parameter of the fluid and transmit a signal to the receiver providing operating instructions for the actuator responsive to the data.

The method may comprise providing the external controller.

Providing the external controller may comprise providing hardware and/or providing software.

In accordance with yet another aspect, there is provided a hydrogen sulfide sensor assembly. The hydrogen sulfide sensor assembly may comprise a housing comprising a plurality of sensors configured to measure concentration of hydrogen sulfide in a vapor phase of the wastewater. The hydrogen sulfide sensor assembly may comprise an actuator configured to selectively fluidly connect or isolate each sensor to the vapor phase of the wastewater. The sensor assembly may comprise a transmitter operably connected to the plurality of sensor and operably connectable to an external controller.

In some embodiments, the housing may comprise a plurality of compartments capable of being reversibly hermetically sealed or fluidly connected to the vapor phase of the wastewater. Each sensor of the plurality of sensors may be positioned in a corresponding compartment of the plurality of compartments. The actuator may be configured to selectively hermetically seal or fluidly connect each compartment of the plurality of compartments.

The disclosure contemplates all combinations of any one or more of the foregoing aspects and/or embodiments, as well as combinations with any one or more of the embodiments set forth in the detailed description and any examples.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
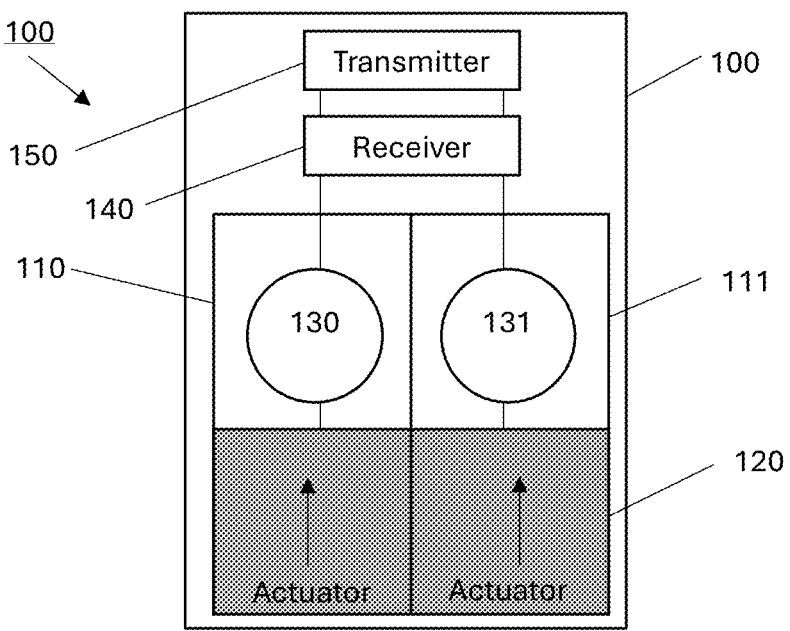
FIG. 1 is a schematic drawing of a sensor assembly, according to one embodiment.

Conduits are used to transport fluids (liquids and/or gases) for long distances through remote locations. Sewage systems, for example, often extend for miles making some portions of the pipeline difficult or impossible to access. Certain parameters of these fluids require periodic or continuous monitoring. Sensors are often positioned within fluid conduits to monitor the fluid remotely. However, it is challenging to repair or replace the remote sensors, and certain sensors require frequent calibration or replacement.

There exists a need for a sensor assembly capable of accurately measuring one or more fluid parameters in a remote location for an extended period of time.

Sewage systems typically include conduits that collect and direct sewage and other waste streams, such as industrial effluents, to a treatment facility. Such systems may include various pumping facilities, such as lift stations, that facilitate the transfer of wastewater to the treatment facilities. The sewage and industrial effluents may contain a high concentration of contaminants to be monitored. During transit, gaseous contaminants may also be generated. Some gaseous contaminants may be odorous species. One problematic gaseous compound formed is hydrogen sulfide ($H_2S$).

Hydrogen sulfide is often formed in wastewater streams when sulfates are converted to sulfides by sulfate reducing bacteria (SRBs) under anaerobic conditions. Hydrogen sulfide is dissolvable in water (up to about 0.4 g/100 ml at 20° C. and 1 atm). In water, hydrogen sulfide exists in equilibrium with the bisulfide ion $HS^-$ and the sulfide ion $S^{2-}$. Unlike sulfide and bisulfide, hydrogen sulfide is volatile, with a vapor pressure of about $1.56 \times 10^4$ mm Hg (2.1 MPa) at 25° C. and may emerge from aqueous solution to form gaseous hydrogen sulfide. The presence of hydrogen sulfide in sewer systems is undesirable due to its offensive odor, toxicity, and corrosivity.

Gaseous hydrogen sulfide exhibits a characteristic unpleasant odor suggestive of rotten eggs. Humans can detect hydrogen sulfide at concentrations as low as 4 ppb. Hydrogen sulfide is considered toxic. Extended exposure to a few hundred ppm can cause unconsciousness and death. Accordingly, the presence of hydrogen sulfide in sewer systems is found objectionable to people who may come into contact with the gaseous effluent from such sewer systems. Furthermore, the release of hydrogen sulfide into the atmosphere is often controlled by regulatory authorities.

Hydrogen sulfide may not only be harmful to humans and other animals but may also be harmful to a sewer system in which it is present. For instance, gaseous hydrogen sulfide present in a sewer system may dissolve into water, which may condense on walls or other surfaces within the sewer system. Once dissolved in the water, sulfuric acid may be formed by oxidation of the dissolved hydrogen sulfide. The sulfuric acid so formed may cause corrosion to metal and concrete structures in or around the sewer system.

Hydrogen sulfide may also support the growth of problematic organisms. Exemplary organisms are thiothrix and beggiatoa. These organisms are associated with bulking problems that occur in activated sludge water treatment systems.

Accordingly, an excessive concentration of hydrogen sulfide is generally undesirable in sewer systems. Hydrogen sulfide may be removed from wastewater by oxidation with additives, such as potassium permanganate, chlorine, and sodium chlorite. Hydrogen sulfide may be driven to equilibrium of nonvolatile forms by addition of a pH adjuster. Sulfide may be removed from wastewater by biochemical oxidation with nitrate solutions. Sulfide may be removed from wastewater by binding with iron salts. Sulfide formation may be inhibited by oxygen injection and nitrate solutions, in amounts effective to inhibit anoxic or anaerobic states. However, to control and/or reduce hydrogen sulfide in a sewer system, the concentration of hydrogen sulfide should be known. Hydrogen sulfide may be remediated by measuring the concentration and dosing the wastewater with an appropriate amount of chemicals.

To measure hydrogen sulfide in sewer systems, $H_2S$ sensors, for example, an electrochemical sensor, is typically positioned within the sewer system, in fluid communication with the source of the wastewater vapor phase gases. As previously mentioned, certain portions of the sewer system may be difficult to access. One common problem is that sensors require maintenance on a routine basis, which can be difficult in a remote location. The relatively short service interval of remote hydrogen sulfide sensors is one of the limiting factors in measuring $H_2S$ concentration. The sensor assemblies and methods disclosed herein may be employed to extend the operating or maintenance schedule of $H_2S$ sensors located in a sewer distribution system.

The systems and methods disclosed herein may refer to sewage systems and hydrogen sulfide gas. However, sewage systems and hydrogen sulfide gas are exemplary embodiments. It should be understood that the systems and methods disclosed herein may be employed to measure any parameter of a remote fluid.

In accordance with one aspect, there is provided a method of monitoring one or more parameter of a fluid, for example, a liquid or a gas, in a remote location. A sensor assembly configured to monitor the fluid is provided herein. The sensor assembly may be deployed to the remote location. The sensor assemblies and methods disclosed herein may provide calibrated measurements of one or more parameter of the fluid for an extended period of time, reducing the need to access the remote location. In exemplary embodiments, the sensor assemblies and methods disclosed herein may extend the operating or maintenance schedule of $H_2S$ sensors located in a sewer distribution system.

As disclosed herein, "remote locations" include locations that are difficult to access due to distance or inconvenience. For example, gaining access to a remote location may be time consuming, require a lot of resources, may be a burden to the community, may be dangerous, or otherwise cumbersome.

The sensor assembly may comprise a housing supporting a plurality of sensors for monitoring at least one parameter of the fluid. The housing may be formed of a material that is water resistant, corrosion resistant, durable, and/or structurally sound. The housing may be constructed and arranged to isolate interior components from the fluid. The housing may be mounted to the location of the fluid by any manner. The housing may comprise an attachment element, for example, a hook, fastener, clasp, buckle, clip, pin, mating feature, or other attachment element. In one exemplary embodiment, the housing may comprise a mating feature attachable to a corresponding mating feature fixed to an interior surface of a manhole cover.

The method may comprise fluidly connecting at least one of the sensors to a source of the fluid. The fluid may be a liquid or a gas. Thus, fluidly connecting the sensor may comprise connecting the sensor to a source of a liquid, such as wastewater. Fluidly connecting the sensor may comprise connecting the sensor to a source of a gas, such as gas in the headspace of a sewage system, for example, a vapor phase of the wastewater. Other liquids and gases are within the scope of the disclosure.

The sensor assembly may be configured to operate the sensors in series. As the operating interval of a first sensor trends to expiration, a second or subsequent sensor may be activated to continue monitoring the fluid. The sensor assembly may activate a second or subsequent sensor responsive to the first sensor becoming spent, damaged, uncalibrated, losing connectivity, or otherwise requiring maintenance. Thus, the sensor assembly may provide substantially uninterrupted service over an extended period of time, reducing the need to access the remote location for service.

As disclosed herein, an "active" sensor may refer to an in-use sensor. The active sensor may be fluidly connected to the source of the fluid. The active sensor may be engaged in measuring the at least one parameter of the fluid.

As disclosed herein, an "inactive" sensor may refer to a sensor that is not currently in use. Inactive sensors may include sensors in the queue to become activated. Inactive sensors may include sensors which were previously active and have been inactivated, for example, due to expiration, damage, or a scheduled inactivation. At least some inactive sensors may be hermetically sealed from the fluid. In particular, inactive sensors in the queue to become activated may be hermetically sealed from the fluid. In some embodiments, inactive sensors which were previously active may be hermetically sealed from the fluid. In other embodiments, inactive sensors which were previously active need not be hermetically sealed from the fluid.

As disclosed herein, "operating interval" of a sensor may refer to a complete service cycle of the sensor. The operating interval of the sensor may expire when the sensor becomes spent. The operating interval of the sensor may expire when a calibration is not effective to correct a drift in measurement accuracy. In some embodiments, a sensor whose operating interval has expired may be repaired or refurbished. However, the operating interval may be expired when the sensor may not be effectively reused without removal from the remote location.

As disclosed herein, the operating interval of the active sensor "trending to expiration" may refer to the active sensor having less than a threshold outstanding operating interval. The threshold outstanding operating interval may be 40%, 35%, 30%, 25%, 20%, 15%, 10%, 5%, 3%, or 1%. For example, the active sensor may be trending to expiration when the outstanding operating interval of the sensor is less than 40%, less than 35%, less than 30%, less than 25%, less than 20%, less than 15%, less than 10%, less than 5%, less than 3%, or less than 1% of the total operating interval of the sensor.

In some embodiments, the sensor assembly may have one active sensor. In some embodiments, the sensor assembly may have more than one active sensor simultaneously, for example, two, three, four, five, six, or more active sensors simultaneously. The remaining sensors may be inactive.

The sensor assembly may comprise an actuator. The actuator may be configured to selectively activate or inactivate each sensor of the plurality of sensors. The actuator may activate or inactivate each sensor by mechanical action. For example, the actuator may be configured to selectively fluidly connect each sensor to the source of the fluid. The actuator may be configured to selectively isolate each sensor from the source of the fluid. In some embodiments, the actuator may be configured to hermetically seal one or more sensors from the source of the fluid. In some embodiments, the sensors may be electrically actuated.

In certain embodiments, the actuator may be configured to selectively activate or inactivate each sensor by electrical action. For example, the sensor assembly may comprise a processor electrically connected to the sensors. The processor may selectively electrically connect or electrically isolate a selected sensor. In some embodiments, the sensor assembly may comprise a plurality of processors. For example, the sensor assembly may comprise a corresponding processor for each sensor. In some embodiments, the sensor assembly may be configured to electrically activate or inactivate selective sensors by activating or inactivating a corresponding processor of the selected sensor.

In some embodiments, the housing may comprise a plurality of compartments capable of being reversibly hermetically sealed or fluidly connected to the fluid. Each sensor may be positioned in a corresponding compartment. The actuator may be configured to selectively hermetically seal or fluidly connect each compartment, thereby sealing or connecting each corresponding sensor. In such embodiments, the actuator may comprise a door, for example, a sliding door. In certain embodiments, the actuator may comprise a hydraulic diverter, for example, a solenoid switch or other valve or series of valves.

In certain exemplary embodiments, the mechanical actuator may comprise one or more disks, each having one or more fluid opening. Each disk may be associated with two or more sensors. The actuator may fluidly connect the selected compartment by arranging the disk to position the fluid opening over the compartment. The assembly may comprise an O-ring or other rubber or polymeric seal or washer to provide a hermetic seal.

In one exemplary embodiment, the compartments may be arranged circumferentially about a central axis of the sensor assembly. The actuator may comprise one or more rotating disks, each having one or more opening. The actuator may comprise a rotating shaft or gear configured to drive the one or more disk to position the fluid opening over the selected compartment, fluidly connecting the compartment. For instance, the actuator may comprise one disk having one fluid opening, configured to selectively fluidly connect one compartment at a time. The actuator may comprise one disk having two fluid openings configured to selectively fluidly connect two compartments simultaneously. The actuator may comprise two disks, each having two fluid openings. Such an arrangement may be used to allow for a selection to fluidly connect one compartment or two compartments simultaneously. Additional arrangements are within the scope of the disclosure, for example, one, two, three, four, five, or six disks may each have independently one, two, three, four, five, or six fluid openings. In certain embodiments, the disk may additionally have a central opening substantially concentric to the central axis of the sensor assembly, for example, to allow for rotational elements.

In some embodiments, the sensor assembly may have one fluidly connected compartment. In some embodiments, the sensor assembly may have more than one fluidly connected compartment simultaneously, for example, two, three, four, five, six, or more fluidly connected compartments simultaneously. The remaining compartments may be hermetically sealed or non-hermetically sealed.

The sensor assembly may comprise a pump configured to direct the fluid to the sensor. The pump may be configured to provide a minimum fluid flow effective to direct fluid to the sensor and expel stagnant fluid from the compartment, away from the sensor.

In some embodiments, the sensor assembly may comprise a humidity capturing media.

The sensor assembly may comprise a power source. For instance, the sensor assembly may comprise at least one battery, for example, at least one rechargeable battery. The power source may be a lithium ion battery. The power source may comprise an electric generator or a natural energy source. The power source may be isolated from the fluid. The power source may be configured to provide power to the sensor assembly and/or its components for at least 3 months, for example, at least 6 months, at least 7 months, at least 9 months, at least 12 months, at least 13 months, at least 18 months, or at least 24 months. In some embodiments, the deployment cycle of the sensor assembly is defined by the life of the power source.

The methods may comprise measuring at least one parameter of the fluid. The methods may comprise measuring the parameter on a data collection interval of every 1 minute to every 20 minutes, for example, every 1 minute to every 10 minutes, or every 1 minute to every 5 minutes. The parameter may include, for example, concentration of a target analyte, temperature, humidity, e.g., relative humidity or absolute humidity, pH, conductivity, oxidation-reduction potential (ORP), and flow rate.

The plurality of sensors may be selected from gas analyzers, temperature sensors, humidity sensors, pH sensors, conductivity sensors, oxidation-reduction potential (ORP) sensors, total suspended solids (TSS) sensors, total dissolved solids (TDS) sensors, liquid chemical sensors, dissolved gas sensors, and flow meters. The sensor may be configured to measure the parameter on a data collection interval every 1 minute to every 20 minutes, for example, every 1 minute to every 10 minutes, or every 1 minute to every 5 minutes.

The parameter may be concentration of a target analyte in a gas. In certain embodiments, the plurality of sensors may be gas analyzers. Exemplary gases that may be detected by the sensors include hydrogen sulfide, benzene, ammonia, carbon monoxide, carbon dioxide, oxygen, and methane. Other gas analyzers are within the scope of the disclosure. The gas analyzer may have a detection limit between 1-20 ppm. For example, the gas analyzer may have a detection limit of about 20 ppm, about 10 ppm, about 5 ppm, about 3 ppm, or about 1 ppm. The gas analyzer may have an accuracy of between ±2% within 1-20 ppm. The gas analyzer may have an accuracy of between ±10% within 21-200 ppm.

The parameter may be concentration of a target analyte in a liquid. For example, the liquid chemical sensor may be a device or instrument that determines the detectable presence, concentration, or quantity of a given analyte in a liquid. Exemplary liquid analytes include liquid ammonia, benzene, toluene, ethylbenzene, xylene. The sensor may be configured to measure concentration of TSS or TDS. Exemplary dissolved gases may include dissolved oxygen, dissolved sulfide, dissolved hydrogen, dissolved $CO_2$, and dissolved methane.

The parameter may be temperature of the fluid. In certain embodiments, the plurality of sensors may comprise at least one temperature sensor. The temperature sensor may have an accuracy of ±2° F. within 32-140° F. or ±1° C. within 0-60° C.

The parameter may be humidity, for example, humidity of a gas. In certain embodiments, the plurality of sensors may comprise at least one humidity sensor. The humidity sensor may have an accuracy of ±4% within 0-100%.

The parameter may be pH. In certain embodiments, the plurality of sensors may comprise at least one pH sensor. The pH sensor may have an accuracy of ±0.2 within 0-14 pH units.

In some embodiments, the plurality of sensors may be configured to selectively measure more than one parameter of the fluid. For example, the sensor assembly may include more than one type of sensor. During operation, at least one sensor of each type may be active simultaneously. In one exemplary embodiment, the sensor assembly may include one or more of gas analyzers, temperature sensors, and pH sensors. In another exemplary embodiment, the sensor assembly may include liquid chemical sensors, temperature sensors, and pH sensors. In yet another exemplary embodiment, the sensor assembly may include ORP sensors and conductivity sensors. In yet another exemplary embodiment, the sensor assembly may include TDS sensors and TSS sensors. Other combinations are within the scope of the disclosure. The methods may include independently activating and/or inactivating sensors of each type as active sensors trend to expiration.

In accordance with another aspect, a sensing system is provided. The sensing system may comprise a sensor assembly and an external controller. Thus, the sensor assembly may be operably connectable to at least one external controller. The sensor assembly may be operably connectable to the external controller through a wireless connection. For example, the sensor assembly may be operably connectable to an external controller by one or more of ultra-high frequency (UHF) radio waves, a cellular network data connection, or a wireless local area network (WLAN). In some embodiments, the sensor assembly is connectable to the external controller when the external controller is within the sensor assembly's wireless personal area network (WPAN). For instance, the external controller may automatically connect to the sensor assembly's WPAN upon entering the network coverage area. In some embodiments, the sensor assembly is connectable to a cloud, for example, by cellular network data connection. The external controller may be connectable to the sensor assembly through the cloud.

The external controller may be a computer or mobile computing device. The external controller may comprise a touch pad or other operating interface. For example, the external controller may be operated through a keyboard, touch screen, track pad, and/or mouse. The external controller may be configured to run software on an operating system known to one of ordinary skill in the art. The external controller may be coupled to a memory storing device, for example, a hard drive, server, or cloud-based memory storage.

The method of monitoring at least one parameter of the fluid may comprise transmitting data from the sensor assembly to the external controller. The method may comprise transmitting data from the sensor assembly to the external controller every 1 hour, every 2 hours, every 3 hours, every 6 hours, every 12 hours, or every 24 hours. Thus, in some embodiments the sensor assembly may comprise a transmitter. The transmitter may be operably connected to the plurality of sensors. The transmitter may be operably connected to the actuator. The transmitter may be operably connected to the power source. The transmitter may be operably connected to the processor and/or a local memory storing device. The local memory storing device may be configured to store data locally until transmission to the external controller. The transmitter may have a communication frequency of 1 hour to 24 hours, for example, 1 hour, 2 hours, 3 hours, 6 hours, 12 hours, or 24 hours. The external controller may comprise a receiver. The external controller may be configured to receive data from the sensor assembly.

The data transmitted from the sensor assembly to the external controller may comprise values for the measured parameter of the fluid. A user may access the data through the external controller. The method may comprise monitoring the data for the measured parameter of the fluid. In some embodiments, the user may monitor the data for the measured parameter. In other embodiments, the external controller may monitor the data for the measured parameter.

The method may further comprise modifying the fluid responsive to the one or more values for the measured parameter exceeding a threshold value. For example, the method may comprise dosing the fluid with at least one treating agent responsive to one or more measurements of the parameter exceeding a threshold value, for example, at least 1 measurement, at least 2 measurements, at least 3 measurements, at least 5 measurements, or more. The measurements may be consecutive measurements or a majority of measurements taken in a pre-determined timespan. The treating agent may comprise, for example, a pH adjuster, an odor or corrosion control agent, a temperature control agent, a conductivity or oxidation reduction control agent, a solids-liquid separation agent, such as a coagulant or a flocculant, and/or a contaminant neutralizer, such as an oxidant or an inhibitor. The fluid may be dosed with an effective amount of the treatment agent may to bring the value for the measured parameter within tolerance of a target value, for example, below the threshold value.

The external controller may be operably connectable to a treating station configured to modify the fluid, as previously described. Thus, the system may comprise a treating station. The treating station may be disposed remotely from the sensor assembly. In some embodiments, the system may comprise a plurality of sensor assemblies positioned remotely from each other and configured to measure the parameter at more than one location. The treating station may be disposed remotely from at least one of the plurality of sensor assemblies. The treating station may be configured to introduce at least one treating agent into the fluid to modify the parameter.

The external controller may be coupled to a memory storing device. The transmitter may be configured to transmit data from the sensor assembly to a memory storing device coupled to the external controller. The memory storing device may comprise a hard drive, server, or cloud-based memory storage device.

The data transmitted from the sensor assembly to the external controller, e.g., values for the measured parameter of the fluid, may be used by the external controller as a control signal for administering at least one treating agent, such as an odor or corrosion control agent, into the fluid. The external controller may include a system processor coupled to a memory device storing an algorithm configured to determine an amount of the at least one treating agent to administer to the fluid based on at least the measured parameter of the fluid. In some embodiments, the algorithm may be configured to define a baseline dose of a treating agent sufficient to bring a concentration of an analyte, e.g., contaminant, e.g., odorous species, e.g., $H_2S$, in the fluid, e.g., a headspace of the sewer system, to be below a predetermined target value, determine a treatment dose of the treating agent based on the baseline dose and an adjustment factor, and generate an output signal that directs the treatment system to administer the at least one treating agent. The adjustment factor to the baseline dose may be determined by the measured parameter of the fluid and data corresponding to at least one environmental variable proximate the sensor assembly.

In some embodiments, the at least one environmental variable may include, but is not limited to, one or more of current time period, outdoor temperature, outdoor relative humidity, wind speed, wind direction, or atmospheric pressure. In further embodiments, the at least one environmental variable further comprises one or more of solar flux, rainfall, lunar cycles, or tidal cycles. In some embodiments, the adjustment factor to the baseline dose further may be determined based on data corresponding to at least one social variable selected from one or more of population demographics, population density, traffic patterns in a region proximate the sewer system, or activity from one or more social media outlets, e.g., FACEBOOK® or TWITTER®. In further embodiments, the adjustment factor may be determined based on data corresponding to at least one of population growth projections, municipal budget, or municipal credit rating from the municipality where the sewer system in located.

In some embodiments, the algorithm comprises a machine learning algorithm. For example, the machine learning algorithm may include a neural network or neural net architecture. The machine learning algorithm may be configured to be trained, e.g., trained to predict the baseline dose of the at least one treating agent, using at least cataloged historical data pertaining to one or more of concentrations of an analyte, e.g., a contaminant, e.g., an odorous species, e.g., $H_2S$, in the fluid, e.g., a headspace of the sewer, cataloged by time period, meteorological data cataloged by time period, cataloged lag times between administration of the treatment dose and changes in the analyte, e.g., $H_2S$, concentrations in a portion of the sewer system, or volume of the at least one treating agent previously administered cataloged by time period. In particular embodiments, the machine learning algorithm may be configured to generate output signals to permit the controller adjust the dose of the at least one treating agent in substantially real time based on measured values of the fluid, the data regarding at least one environmental variable, and the data regarding at least one social variable.

Other treatment schemes are within the scope of the disclosure, for example, adjustment of pH, temperature, conductivity, oxidation-reduction potential, and/or presence of another analyte, e.g., contaminant, in the fluid with an algorithm as previously described.

The data transmitted from the sensor assembly to the external controller may comprise signals indicative of the status of one or more of the actuator, sensors, compartments, and/or power source of the sensor assembly. The data may comprise independent signals for each sensor and/or compartment. For instance, the signals may inform the external controller which sensors are active or inactive, the outstanding operating interval of each sensor, whether the inactive sensors are in queue or taken out of service, the position of the actuator, which compartments are open or closed, and/or a lifetime of the power source. The user may be informed of the status of the components through the external controller.

The method may comprise alerting a user responsive to an indication of a need to repair or replace the sensor assembly or a component thereof. In some embodiments, the external controller may be configured to alert a user responsive to an indication of a need to repair or replace the sensor assembly or a component of the sensor assembly. For instance, the external controller may be configured to alert a user responsive to the signal from the sensor assembly indicating that the actuator, a sensor, a compartment, and/or power source requires repair or replacement. In some embodiments, the external controller may be configured to determine whether there is a need to repair or replace the sensor assembly or component thereof, for example, responsive to data received from the sensor assembly. Repair may include regular maintenance, unplanned maintenance, or unanticipated maintenance.

The method may comprise alerting a user that the power source is close to depletion. In certain embodiments, the external controller may be configured to alert a user responsive to the signal indicating that the power source is close to depletion. The methods may comprise alerting a user when the power source has less than 40% remaining lifetime, less than 30% remaining lifetime, less than 20% remaining lifetime, less than 10% remaining lifetime, or less than 5% remaining lifetime. The methods may comprise alerting a user when the power source has less than 31 days remaining estimated lifetime, less than 20 days remaining estimated lifetime, less than 10 days remaining estimated lifetime, less than 7 days remaining estimated lifetime, less than 5 days remaining estimated lifetime, or less than 3 days remaining estimated lifetime.

The user may be alerted by a visual, auditory, and/or tactile alarm emitted by the external controller or directed by the external controller. The user may be alerted by an electronic mail message and/or text message. The user may be alerted by a push notification, for example, displayed by the external controller or transmitted by the external controller. In some embodiments, the external controller may transmit a push notification to a mobile device associated with the user.

The external controller may be capable of transmitting a firmware update to the sensor assembly processor. The external controller may be capable of transmitting instructions for a data collection interval to the plurality of sensors. For example, the method may comprise selecting a data collection interval for the parameter of the fluid. The external controller may be configured to instruct the plurality of sensors to collect data based on the selected data collection interval. The external controller may be capable of transmitting instructions to modify the data collection interval. The external controller may be configured to determine the data collection interval.

The external controller may be configured to determine an operating interval of at least one sensor, for example, an active sensor. The external controller may process data transmitted by the sensor assembly and/or stored on the memory storing device to determine the operating interval of the sensor. For instance, the external controller may determine the operating interval of the active sensor responsive to receiving data including values for the parameter being measured, and optionally, stored data including values for the parameter measured over time. In certain embodiments, the external controller may use historical data from previous similar sensors to determine the operating interval of the active sensor.

The data transmitted from the sensor assembly to the external controller, e.g., values for the measured parameter of the fluid, may be used by the external controller as a control signal for instructing the actuator to activate an inactive sensor. The external controller system processor may store an algorithm configured to determine the operating interval of the active sensor. In some embodiments, the algorithm comprises a machine learning algorithm. For example, the machine learning algorithm may include a neural network or neural net architecture. The machine learning algorithm may be configured to be trained, e.g., trained to predict the approximate operating interval of the active sensor, using at least cataloged historical data pertaining to one or more operating intervals of previous similar sensors, values for the measured parameter, and/or environmental factors having an effect on the operating interval of the sensor.

In one exemplary embodiment, the parameter may be or include concentration of a target analyte, for example, concentration of hydrogen sulfide in a gas. The active sensor may trend to expiration at a faster rate responsive to greater concentrations of hydrogen sulfide being detected. The external controller may determine the operating interval of the sensor based on the amount of hydrogen sulfide detected during the active period of the sensor. The external controller may consider the operating interval and activity of previous sensors to determine the operating interval of the present active sensor.

The external controller may be configured to transmit a signal to the sensor assembly. Thus, the sensor assembly may comprise a receiver. The receiver may be operably connected to one or more component of the sensor assembly, for example, the actuator and the sensors. The receiver may be operatively connected to the processor. The receiver may be operably connectable to the external controller.

The external controller may be configured to provide operating instructions to the sensor assembly responsive to the data received from the sensor assembly and/or data stored on the memory storing device. For instance, the external controller may be configured to transmit a signal to the sensor assembly comprising instructions to activate or inactivate select sensors. The signal may include instructions to inactivate an active sensor that is trending to expiration and/or activate an inactive sensor. The newly activated sensor may replace the newly inactivated sensor. The newly activated sensor may be employed to check or confirm measurements obtained by the active sensor. In other embodiments, the newly activated sensor may be employed to calibrate the active sensor.

The external controller may be configured to transmit a signal to the sensor assembly comprising instructions to operate the actuator. The method may comprise operating the actuator to fluidly connect an inactive sensor. The method may comprise operating the actuator to seal, optionally hermetically seal, an active sensor. For example, the actuator may be operated responsive to the external controller determining the operating interval of an active sensor is trending to expiration. The actuator may fluidly connect a previously inactivated sensor to replace a newly inactivated sensor, to check or confirm measurements taken by an active sensor, or to calibrate another active sensor. Thus, in some embodiments, the actuator may be configured to operate responsive to the sensor assembly receiving a signal from the external controller.

In some embodiments, the actuator may be configured to operate on a pre-determined schedule. The pre-determined schedule may be set by a user. The pre-determined schedule may be regulated by the external controller. For example, the external controller may transmit a signal to the actuator comprising instructions to fluidly connect an inactive sensor or seal an active sensor on a pre-determined schedule. In other embodiments, the pre-determined schedule may be programmed into the actuator or sensor assembly, for example, into the processor.

The pre-determined schedule may be selected based on the type of sensor being utilized. In some embodiments, the pre-determined schedule may be selected based on historical data from previous similar sensors. The pre-determined schedule may be revisited periodically with recent data and updated if the recent data shows any significant changes. For example, the pre-determined schedule may be revisited and/or updated weekly, monthly, bi-monthly, quarterly, every six months, or annually.

The pre-determined schedule may be selected to provide substantially uninterrupted sensing service for a pre-determined period of time. For instance, the pre-determined schedule for each sensor may be selected based on a number of sensors in the assembly, to provide substantially uninterrupted service for at least 3 months, at least 6 months, at least 9 months, at least 12 months, at least 18 months, or at least 24 months.

In some embodiments, the number of sensors may be selected to provide substantially uninterrupted sensing service for a predetermined period of time. For instance, the number of sensors may be selected based on an approximate operating interval of each sensor, to provide substantially uninterrupted service for at least 3 months, at least 6 months, at least 9 months, at least 12 months, at least 18 months, or at least 24 months. The approximate operating interval of the sensor may be the theoretical service life of the sensor, for example, as indicated by the manufacturer.

In one exemplary embodiment, the sensor assembly may contain two sensors having an approximate operating interval each of over six months, to provide substantially uninterrupted service for at least 12 months. The pre-determined actuator schedule may be selected to activate a new sensor every six months. In another exemplary embodiment, the sensor assembly may contain four sensors having an approximate operating interval each of over three months, to provide substantially uninterrupted service for at least 12 months. The pre-determined actuator schedule may be selected to activate a new sensor every three months. In another exemplary embodiment, the sensor assembly may contain six sensors having an approximate operating interval each of over two months, to provide substantially uninterrupted service for at least 12 months. The pre-determined actuator schedule may be selected to activate a new sensor every two months. Other arrangements and pre-determined operating times are within the scope of the disclosure.

The pre-determined schedule may be selected to include a service buffer period. For example, the pre-determined schedule may be selected to allow for activation of a new sensor before the approximate operating interval of the previous sensor elapses. The buffer period may include, for example, about 1% to 25% of the approximate operating interval of the active sensor, for example, about 5% to 20% of the approximate operating interval, or about 5% to 15% of the approximate operating interval of the sensor. The service buffer period may provide a failure backup for the sensor assembly. For example, an inactivated sensor having at least 5% remaining operating interval may be activated responsive to an indication of failure from one or more remaining sensors.

The method may comprise alerting a user that the operating interval of an active sensor is trending to expiration. For example, the method may comprise alerting a user responsive to the external controller determining the operating interval of an active sensor is trending to expiration. The external controller may be configured to alert the user that the operating interval of the active sensor is trending to expiration. The methods may comprise alerting a user when the operating interval of the active sensor is less than 40%, less than 30%, less than 20%, less than 10%, or less than 5%. The methods may comprise alerting a user when the operating interval of the active sensor is estimated to be less than 31 days, less than 20 days, less than 10 days, less than 7 days, less than 5 days, or less than 3 days.

In certain embodiments, an inactive sensor may be activated prior to the presently activated sensor trending to expiration. For instance, the method may comprise activating an alternate sensor or operating the actuator to fluidly connect an alternate sensor prior to the external controller determining the operating interval of an active sensor is trending to expiration or prior to the pre-determined scheduled time for inactivation of the active sensor.

The alternate sensor may be activated to confirm values from an active sensor. Thus, the method may comprise measuring the parameter with another sensor and comparing the new measurement to a measurement taken by an active sensor. The alternate sensor may be activated to calibrate an active sensor. Thus, the method may comprise calibrating an active sensor with a measurement taken by another sensor. The method may comprise calibrating a newly activated sensor with a measurement taken by an active sensor. Additional embodiments exist in which multiple sensors are active and fluidly connected to the source of the fluid simultaneously.

In some embodiments, measurements taken by the active sensor may be compared with measurements taken by an alternate sensor on a pre-determined schedule. The alternate sensor may be activated to check or confirm recent measurements taken by the active sensor. The measurement check may be performed, for example, daily, every 2 days, every 3 days, every 4 days, every 5 days, every 6 days, every 7 days, every 14 days, every 21 days, every 28 days, or more.

In some embodiments, the alternate sensor may be activated to check or confirm recent measurements taken by the active sensor responsive to the active sensor taking a measurement outside a pre-determined tolerance. The pre-determined tolerance may be defined by the accuracy of the sensor as previously described. In some embodiments, the pre-determined tolerance may be at least 10%, at least 5%, at least 3%, at least 1%, or at least 0.1% of the expected theoretical measurement. The expected theoretical measurement may be calculated based on historical data. The external controller may be configured to instruct the actuator to activate an inactive sensor responsive to the active sensor taking a measurement outside the pre-determined tolerance. The method may comprise alerting a user that the active sensor has taken a measurement outside the pre-determined tolerance.

In some embodiments, the alternate sensor may be activated to check or confirm recent measurements taken by the active sensor responsive to the recent measurements exceeding a threshold value that triggers treatment of the fluid. For example, the method may comprise checking the measured parameter with an alternate sensor prior to modifying the fluid. The method may comprise modifying the fluid responsive to a majority of the values for the measured parameter taken by more than one sensor exceeding a threshold value. For example, the method may comprise dosing the fluid with at least one treating agent responsive to a majority of the values for the measured parameter taken by more than one sensor exceeding a threshold value. The method may comprise alerting a user that the measured parameter exceeds a threshold value prior to modifying the fluid.

In some embodiments, calibration measurements may be performed on a pre-determined schedule. An alternate sensor may be activated to calibrate an active sensor. An active sensor may be used to calibrate a newly activated sensor. A calibration may be performed, for example, daily, every 2 days, every 3 days, every 4 days, every 5 days, every 6 days, every 7 days, every 14 days, every 21 days, every 28 days, or more.

In some embodiments, the external controller may be configured to determine whether the active sensor is experiencing drift. Sensors may generally experience drift after about 2-3 weeks of substantially uninterrupted service. The external controller may determine whether the active sensor is experiencing drift responsive to the measurements obtained by the active sensor and historical data for the parameter. The external controller may be configured to alert a user when the active sensor is experiencing drift.

The external controller may be configured to instruct the actuator to initiate a calibration of the active sensor responsive to a determination that the active sensor is experiencing drift. For example, the external controller may be configured to instruct the actuator to initiate a calibration responsive to the measurement being outside tolerance for an expected theoretical measurement. Tolerance may be defined by the accuracy of the sensor as previously described. In some embodiments, tolerance may be at least 10%, at least 5%, at least 3%, at least 1%, or at least 0.1% of the expected theoretical measurement. The expected theoretical measurement may be calculated based on historical data. The method may comprise alerting a user that the active sensor is experiencing drift.

In some embodiments, the external controller system processor may store one or more algorithm, as previously described, configured to determine the pre-determined schedule for operation of the actuator, the pre-determined schedule for checking or confirming a measurement obtained by the active sensor, the pre-determined schedule for calibration, and/or the expected theoretical measurement of the parameter. The algorithm may be trained based on historical data, available public data, and environmental factors.

The method may comprise alerting a user that the operating interval of a last active sensor is trending to expiration. For example, the method may comprise alerting a user responsive to the external controller determining the operating interval of a last active sensor is trending to expiration. The method may comprise collecting the deployed sensor assembly from the remote location. The method may comprise deploying a substitute sensor assembly to the remote location.

Referring to FIG. 1, an exemplary sensor assembly 1000 is shown. Sensor assembly 1000 contains a housing 100 having a plurality of compartments 110, 111. Sensor assembly 1000 contains an actuator 120 configured to seal or fluidly connect compartments 110, 111. Sensor assembly 1000 contains sensors 130, 131 positioned in corresponding compartments 110, 111, respectively. Sensor assembly 1000 contains a receiver 140 operably connected to actuator 120 and sensors 130, 131. Receiver 140 is operably connectable to an external controller (not shown in FIG. 1). Sensor assembly 1000 contains a transmitter 150 operably connected to the actuator 120 and sensors 130, 131. Transmitter 150 is operably connectable to an external controller. For example, transmitter 150 is operably connectable to a memory storing device coupled to the external controller.

Figure 2:
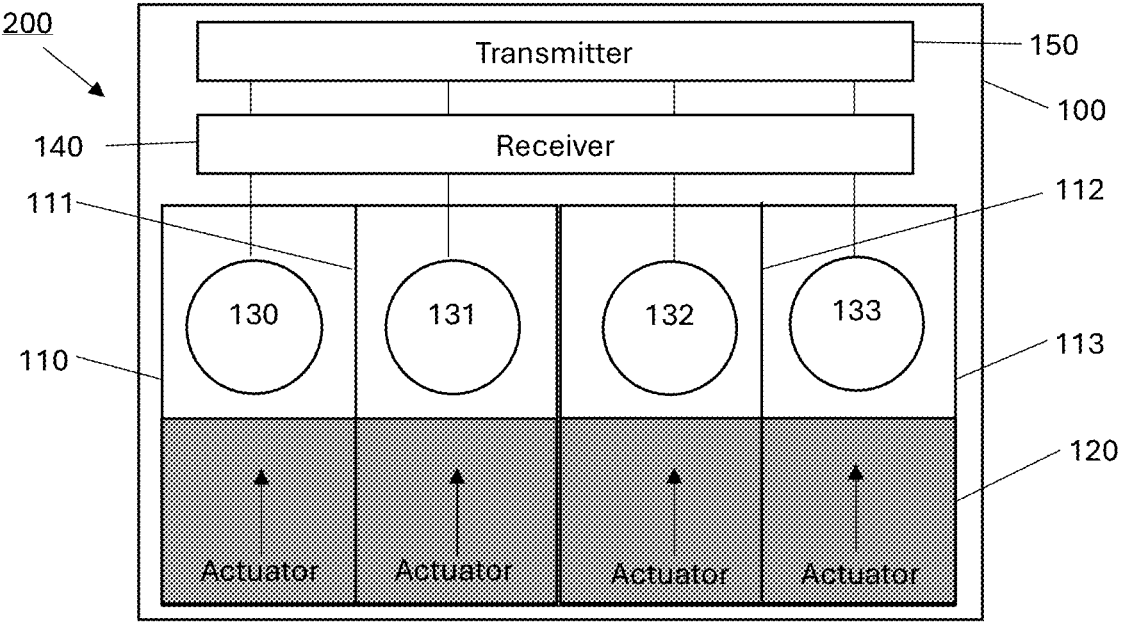
FIG. 2 is a schematic drawing of a sensor assembly, according to one embodiment.

Referring to FIG. 2, an alternate exemplary sensor assembly 2000 is shown. Sensor assembly 2000 is similar to sensor assembly 1000, except that it contains four compartments 110, 111, 112, 113. Each compartment 110, 111, 112, 113 contains a sensor 130, 131, 132, 133, respectively. Actuator 120 is configured to seal or fluidly connect compartments 110, 111, 112, 113. Receiver 140 and transmitter 150 are operably connected to sensors 130, 131, 132, 133. Additional sensor assemblies within the scope of the disclosure may comprise more or less than four compartments and corresponding sensors. For example, the sensor assembly may comprise two, three, four, five, six, seven, eight, nine, ten, eleven, twelve or more compartments and corresponding sensors.

Figure 3:
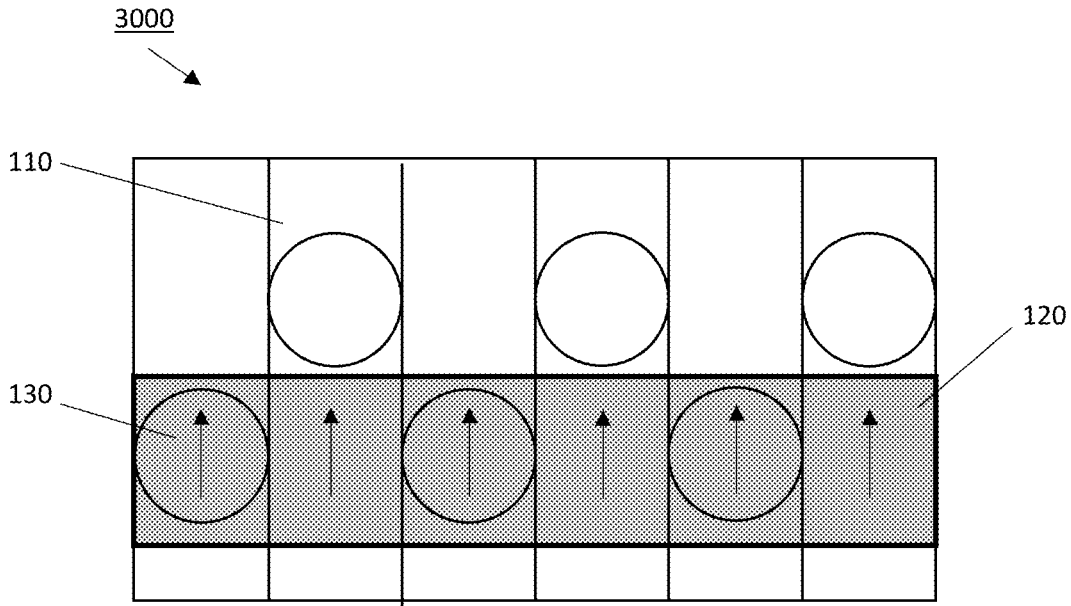
FIG. 3 is a schematic drawing of a sensor assembly, according to one embodiment.

Referring to FIG. 3, an alternate exemplary sensor assembly 3000 is shown. Sensor assembly 3000 contains six compartments 110 and six sensors 130. Actuator 120 comprises a plurality of solenoid switches. Actuator 120 is configured to independently seal or fluidly connect compartments 110.

Figure 4:
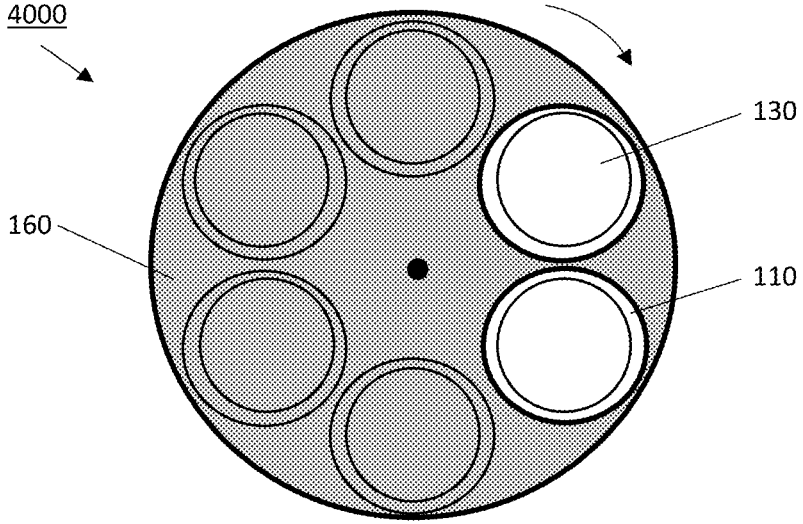
FIG. 4 is a schematic drawing of a sensor assembly, according to one embodiment.

Referring to FIG. 4, an alternate exemplary sensor assembly 4000 is shown. Sensor assembly 4000 is similar to sensor assembly 3000, except that the six compartments 110 are arranged circumferentially about a central axis of sensor assembly 4000. The actuator comprises a first disk 160 having two openings and a second disk (not visible in FIG. 4) having two openings. The disks are configured to independently rotate about the central axis. In some embodiments, one or more disk may additionally have a central opening substantially concentric with the central axis. When the disks are aligned as shown, two compartments are fluidly connected to the source of the fluid. The disks may be circumferentially offset such that only one compartment is fluidly connected to the source of the fluid. Additionally, the disks may be circumferentially offset such that no compartment is fluidly connected to the source of the fluid.

Figure 5:
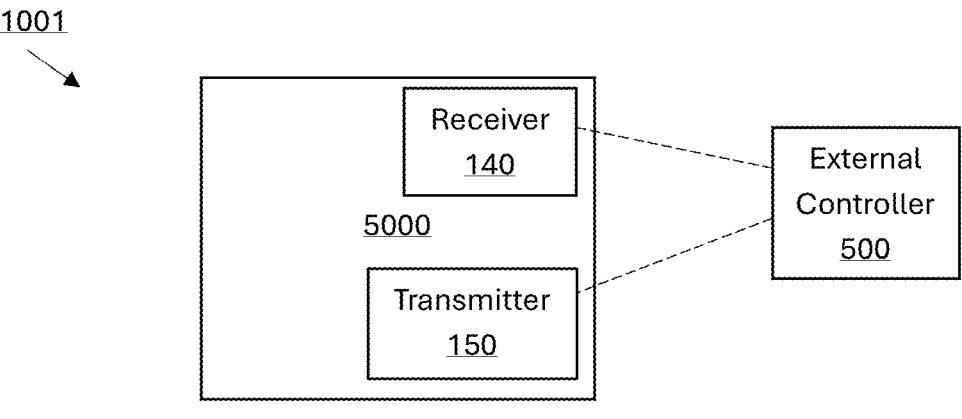
FIG. 5 is a box diagram of a sensing system, according to one embodiment.

Referring to FIG. 5, an exemplary sensing system 1001 is shown. Sensing system 1001 includes sensor assembly 5000 and external controller 500. External controller 500 may be operably connected to sensor assembly 5000 by receiver 140 and/or transmitter 150.

Figure 6:
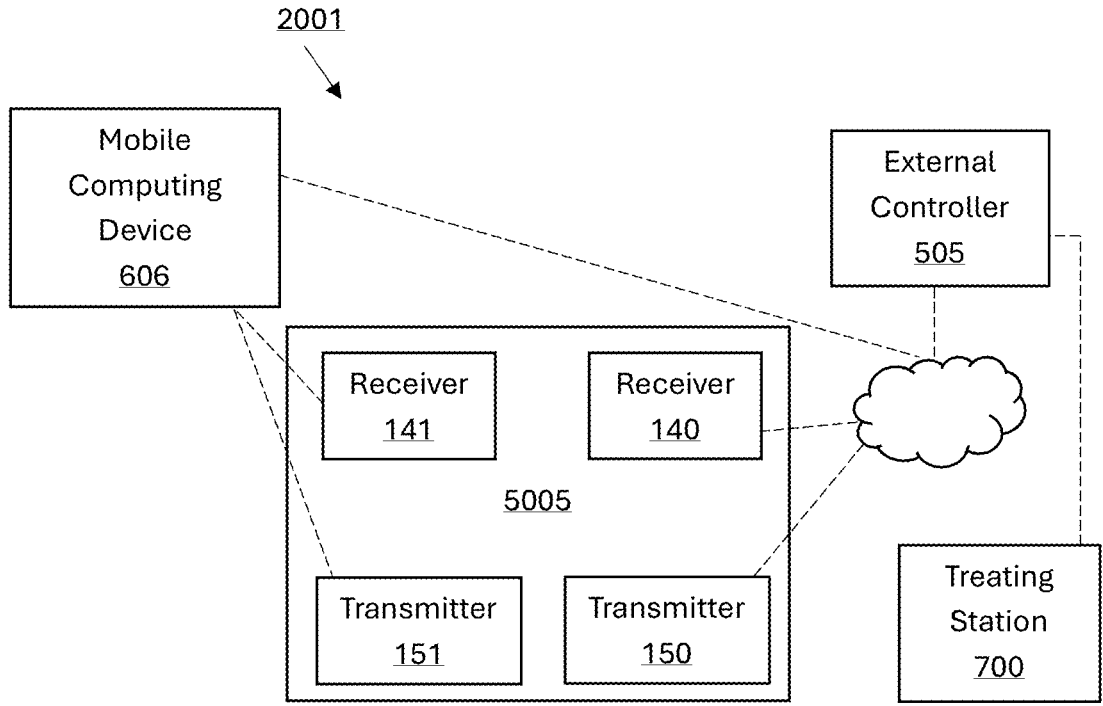
FIG. 6 is a drawing of a sensing system, according to one embodiment.

Referring to FIG. 6, an exemplary sensing system 2001 is shown. Sensing system 2001 includes sensor assembly 5005 and external controller 505. External controller 505 may be operably connected to sensor assembly 5005 by receiver 140 and/or transmitter 150. A mobile computing device 606 may be operably connectable to external controller 505. Mobile computing device 606 may also be operably connectable to the sensor assembly 5005 by receiver 141 and/or transmitter 151. External controller 505 may be operably connectable to treating station 700. Receiver 140 and transmitter 150 may comprise a GSM antenna, cellular CAT M module, and a Sim card. External controller 505 may be a computer. Receiver 141 and transmitter 151 may comprise a QI-wireless power communication module. In some embodiments, a plurality of sensor assemblies 5005 may be included in the system and operably connectable to the external controller 505 and, optionally, mobile computing device 606 as shown in FIG. 6.

Figure 7A:
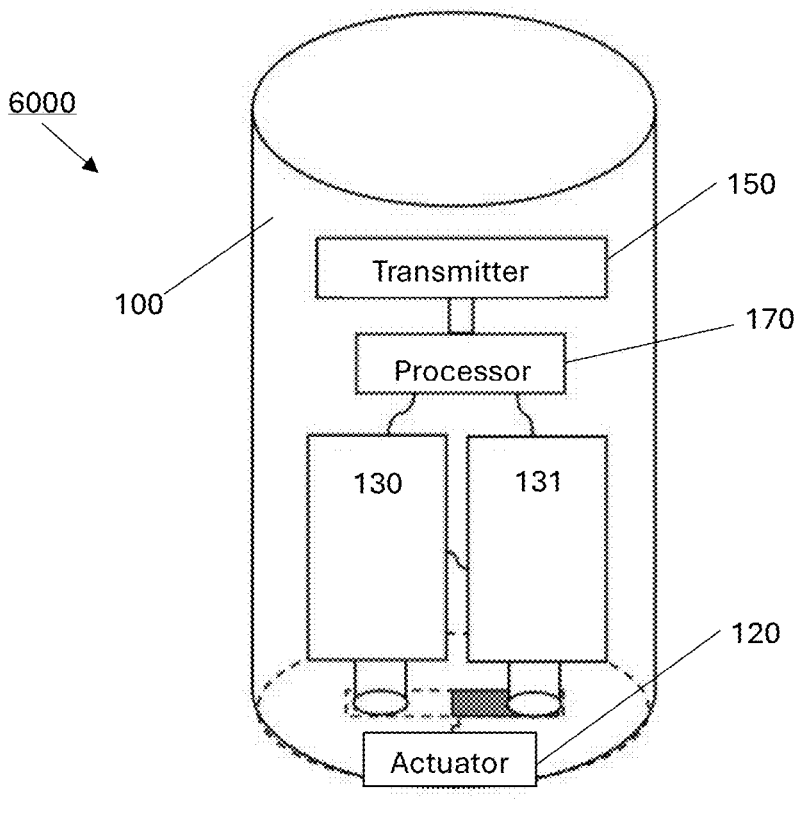
FIG. 7A is a side view of a sensor assembly, according to one embodiment.
Figure 7B:
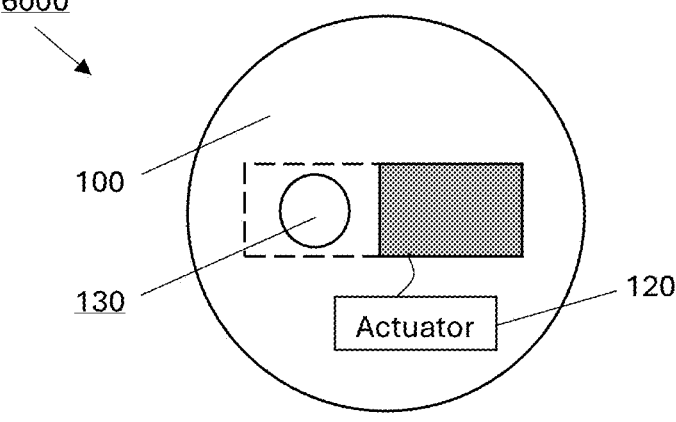
FIG. 7B is a bottom view of the sensor assembly of FIG. 7A.

Referring to FIGS. 7A-7B, exemplary sensor assembly 6000 is shown. Sensor assembly 6000 includes housing 100, sensors 130, 131, actuator 120, and transmitter 150, as previously described. Sensor assembly 6000 further includes processor 170 electrically connected to sensors 130, 131 and transmitter 150. Actuator 120 of sensor assembly 6000 is a solenoid switch. When the active sensor, for example, sensor 130, is trending to expiration, solenoid actuator 120 may seal sensor 130 and expose sensor 131 to the process gas. Processor 170 may electrically connect sensor 131, and the data from sensor 131 may be fed to processor 170 and transmitter 150. FIG. 7A is a side view of sensor assembly 6000. FIG. 7B is a bottom view of sensor assembly 6000. In another embodiment, the sensor assembly may include a plurality of processors, each electrically connected to a corresponding sensor and the transmitter.

Figure 8A:
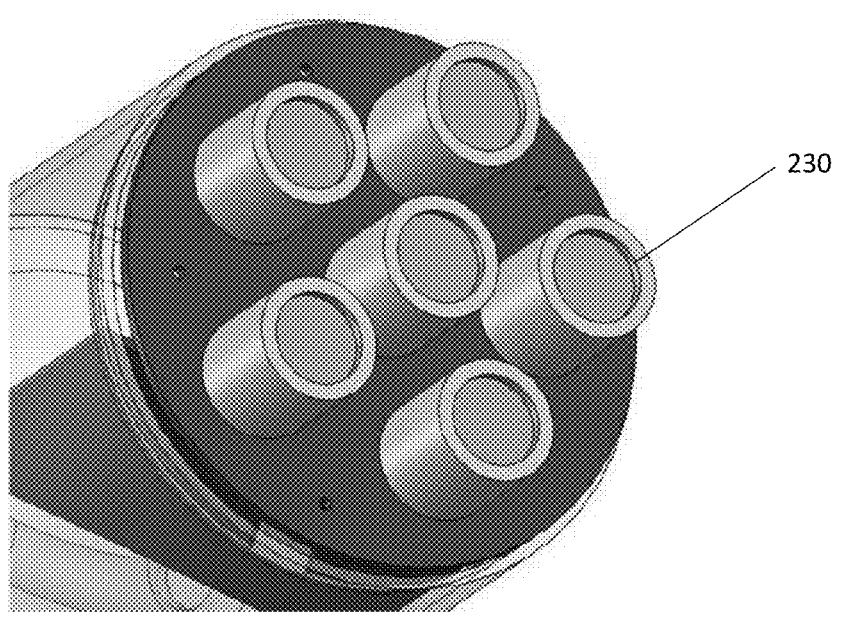
FIG. 8A is a drawing of a partial sensor assembly, according to one embodiment.
Figure 8B:
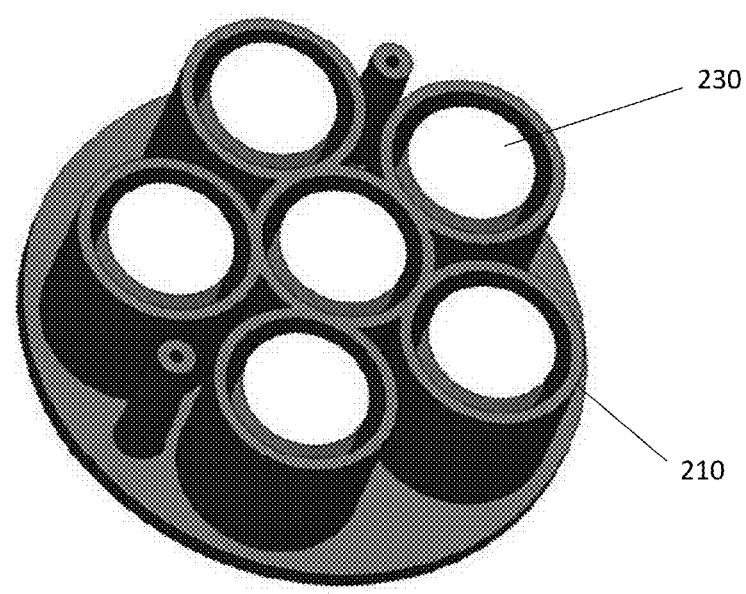
FIG. 8B is a drawing of another portion of the sensor assembly of FIG. 8A, according to one embodiment.
Figure 8C:
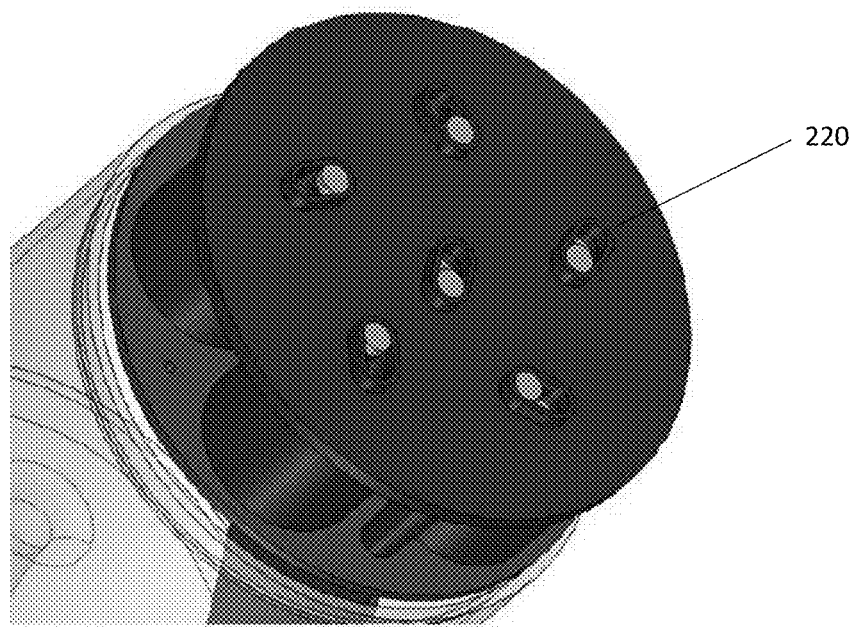
FIG. 8C is a drawing of another portion of the sensor assembly of FIGS. 8A-8B, according to one embodiment.

Referring to FIGS. 8A-8C, a partial view of a sensor assembly is shown. In FIG. 8A, the sensors 230 are shown on a bottom surface of the sensor assembly. In FIG. 8B, sensors 230 in compartments 210 are shown. In FIG. 8C, actuator valves 220 are shown, positioned to fluidly connect or isolate each sensor 230 (not visible in FIG. 8C). In the exemplary assembly of FIGS. 8A-8C, each sensor 230 and compartment 210 has a corresponding actuator valve 220. Valves 220 may be independently operated.

Figure 9:
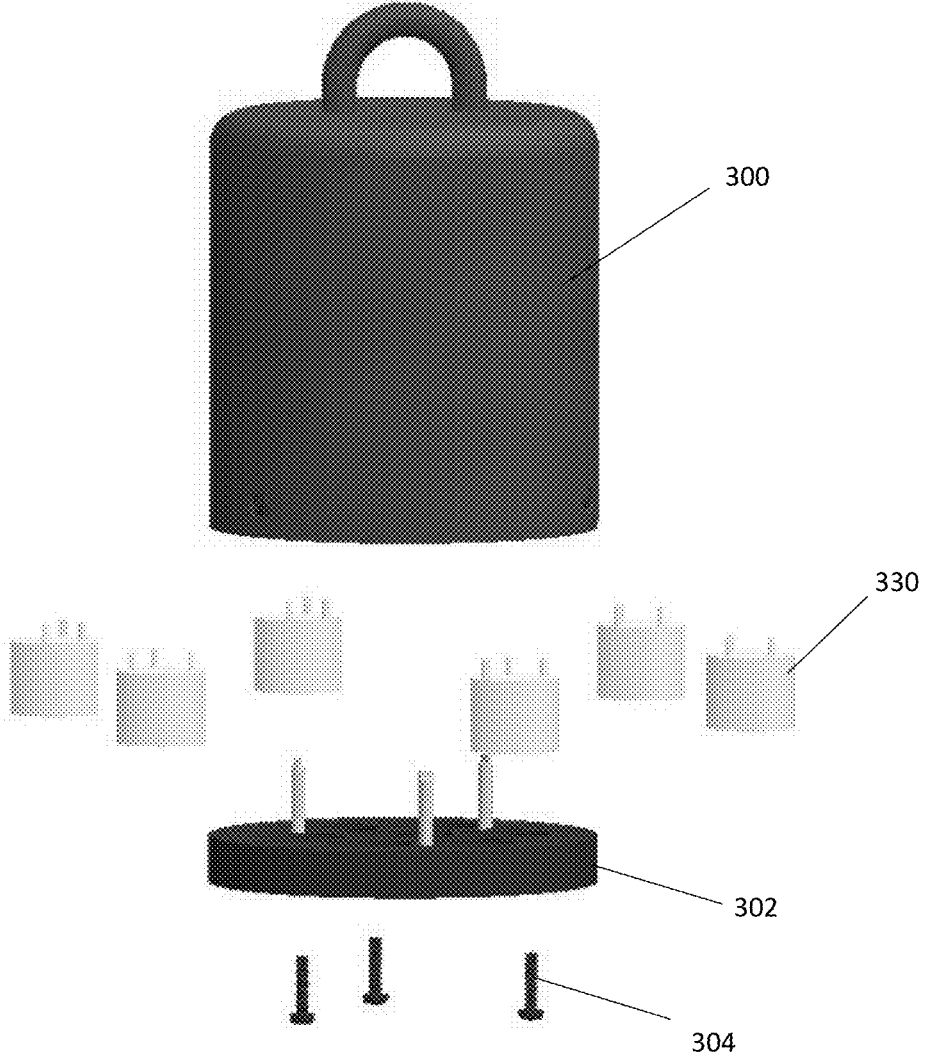
FIG. 9 is an expanded view of a sensor assembly, according to one embodiment.

Referring to FIG. 9, an exploded view of a sensor assembly is shown. The sensor assembly includes housing 300, sensors 330, and housing cover 302. The housing 300 and/or housing cover 302 may have a screw thread for securing the housing cover 302 to the housing 300. The housing cover 302 may additionally be secured by screws 304.

Figure 10:
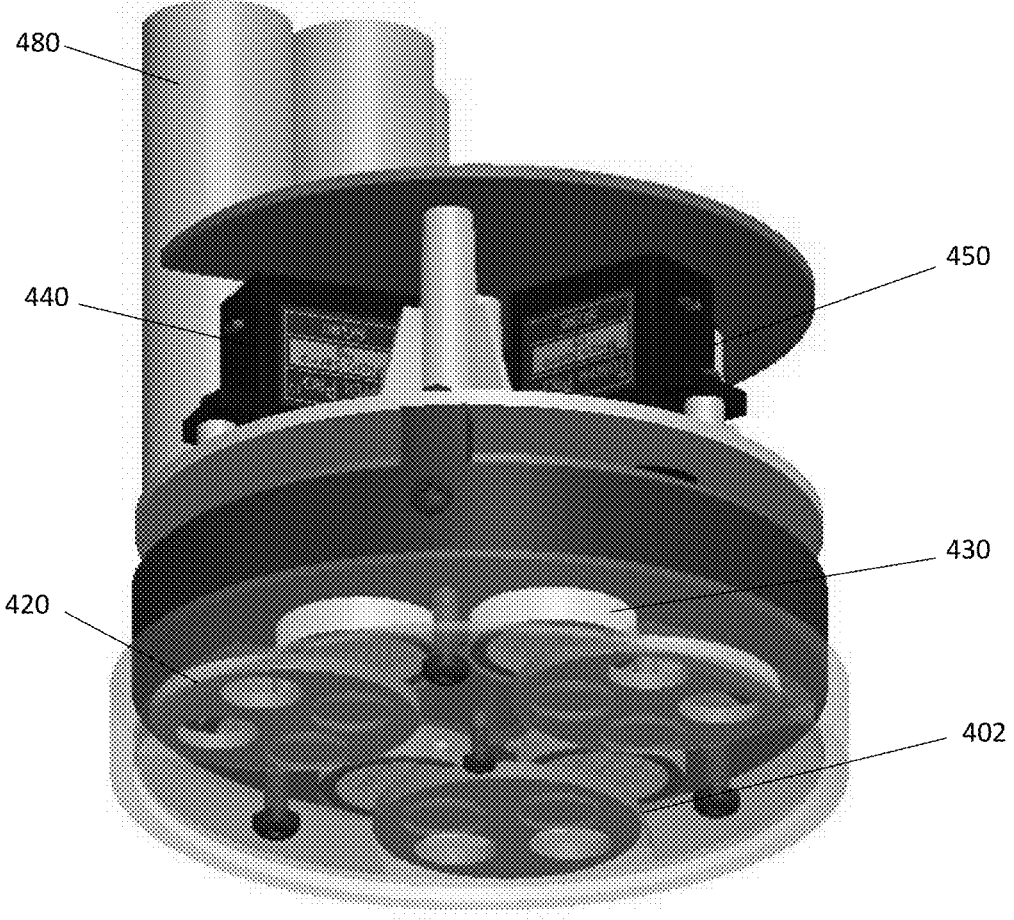
FIG. 10 is a drawing of a partial sensor assembly, according to one embodiment.

Referring to FIG. 10, a partial view of a sensor assembly is shown. The sensor assembly includes sensors 430, power source 480, receiver 440, transmitter 450, and actuators 420 fit onto housing cover 402. Actuators 420 are rotating disks having two openings each. Actuators 420 are laterally arranged in the exemplary sensor assembly of FIG. 10. Each rotating disk actuator 420 is associated with two corresponding sensors 430. Each rotating disk actuator 420 may selectively fluidly connect 0, 1, or 2 sensors 430.

In other embodiments, rotating disk actuators may be vertically stacked over the sensors. For example, such that each vertically stacked rotating disk actuator is associated with all sensors.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure and are intended to be within the scope of the invention. Accordingly, the foregoing description and drawings are by way of example only.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed.

What is claimed is:

1. A sensor assembly configured to be deployed to a source of a fluid at a remote location, comprising:
   a housing comprising a plurality of compartments capable of being reversibly hermetically sealed or fluidly connected to the source of the fluid, when the plurality of compartments are not hermetically sealed;

an actuator configured to selectively hermetically seal or fluidly connect each compartment of the plurality of compartments;
   a plurality of sensors configured to measure a parameter of the fluid, each sensor of the plurality of sensors positioned in a corresponding compartment of the plurality of compartments; and
   a transmitter operably connected to the plurality of sensors, the transmitter being operably connectable to an external controller.

2. The sensor assembly of claim 1, wherein each of the plurality of sensors are gas analyzers.

3. The sensor assembly of claim 2, wherein the gas analyzers are configured to measure concentration of at least one of hydrogen sulfide, benzene, ammonia, carbon monoxide, carbon dioxide, oxygen, and methane in the fluid.

4. The sensor assembly of claim 1, wherein the plurality of sensors are independently selected from gas analyzers, temperature sensors, humidity sensors, ph sensors, conductivity sensors, oxidation-reduction potential (ORP) sensors, total suspended solids (TSS) sensors, total dissolved solids (TDS) sensors, liquid chemical sensors, dissolved gas sensors, and flow meters.

5. The sensor assembly of claim 1, having one compartment fluidly connected to the source of the fluid.

6. The sensor assembly of claim 1, having more than one compartment fluidly connected to the source of the fluid.

7. The sensor assembly of claim 6, wherein the plurality of sensors are configured to selectively measure more than one parameter of the fluid.

8. The sensor assembly of claim 1, being operably connectable to the external controller by one or more of ultra-high frequency (UHF) radio waves, a cellular network data connection, and a wireless local area network (WLAN).

9. The sensor assembly of claim 1, wherein the actuator is configured to operate on a pre-determined schedule.

10. The sensor assembly of claim 1, wherein the transmitter is configured to transmit data from the plurality of sensors to a memory storing device coupled to the external controller.

11. The sensor assembly of claim 1, further comprising a receiver operably connected to the actuator and operably connectable to the external controller, wherein the actuator is configured to operate responsive to the receiver receiving a signal from the external controller.

12. A method of monitoring a parameter of a fluid in a remote location, the method comprising:
   deploying a sensor assembly to the remote location, the sensor assembly comprising a plurality of sensors configured to measure the parameter of the fluid and an actuator configured to selectively hermetically seal or fluidly connect each sensor to the fluid, when the plurality of sensors are not hermetically sealed;
   fluidly connecting at least one first sensor of the plurality of sensors to the fluid to measure the parameter of the fluid;
   transmitting to an external controller data comprising values for the measured parameter of the fluid, the external controller configured to determine an operating interval of the at least one first sensor responsive to the data; and
   operating the actuator to fluidly connect at least one second sensor of the plurality of sensors to the fluid on a pre-determined schedule or responsive to the external controller determining the operating interval of the at least one first sensor is trending to expiration.

13. The method of claim 12, further comprising monitoring the data for the measured parameter of the fluid.

14. The method of claim 13, further comprising modifying the fluid responsive to the values for the measured parameter exceeding a threshold value.

15. The method of claim 12, comprising operating the actuator to fluidly connect the at least one second sensor to the fluid prior to the pre-determined schedule or the external controller determining the operating interval of the at least one first sensor is trending to expiration.

16. The method of claim 15, comprising calibrating the at least one first sensor with a measurement taken by the at least one second sensor.

17. The method of claim 12, further comprising alerting a user responsive to the external controller determining the operating interval of at least one last sensor is trending to expiration.

18. The method of claim 12, further comprising collecting the deployed sensor assembly from the remote location and deploying a substitute sensor assembly to the remote location.

19. A sensing system, comprising:

a sensor assembly comprising:

a housing comprising a plurality of compartments capable of being reversibly hermetically sealed or fluidly connected to a source of a fluid, when the plurality of compartments are not hermetically sealed, an actuator configured to selectively hermetically seal or fluidly connect each compartment of the plurality of compartments, a plurality of sensors configured to measure a parameter of the fluid, each sensor of the plurality of sensors positioned in a corresponding compartment of the plurality of compartments, a transmitter operably connected to the plurality of sensors, and a receiver operably connected to the actuator; and an external controller operably connectable to the transmitter and the receiver, the external controller configured to receive data from the transmitter comprising values for the measured parameter of the fluid and transmit a signal to the receiver providing operating instructions for the actuator responsive to the data.

20. The sensing system of claim 19, wherein the external controller is a mobile computing device.

21. The sensing system of claim 20, wherein the mobile computing device is connectable to the sensor assembly by at least one of ultra-high frequency (UHF) radio waves, a wireless local area network (WLAN), and a cellular network data connection.

22. The sensing system of claim 21, wherein the mobile device is configured to automatically connect to the transmitter upon entering the wireless personal area network (WPAN) of the receiver.

23. The sensing system of claim 19, wherein the sensor assembly and the external controller are connectable to a cloud.

24. The sensing system of claim 23, wherein the sensor assembly is connectable to the cloud by a cellular network data connection.

25. The sensing system of claim 19, wherein the external controller is configured to alert a user responsive to the data indicating a need to repair or replace the sensor assembly or one or more components thereof.

26. The sensing system of claim 19, wherein the external controller is configured to alert a user responsive to the values for the measured parameter exceeding a threshold value or being outside tolerance of an expected theoretical measurement.

27. The sensing system of claim 19, wherein the external controller is connectable to a treating station disposed remotely from the sensor assembly and configured to modify the fluid responsive to the values for the measured parameter.

28. The sensing system of claim 19, wherein each of the plurality of sensors is configured to measure concentration of a target analyte in the fluid.

\* \* \* \* \*